(12) United States Patent
Rush

(10) Patent No.: US 7,745,132 B1
(45) Date of Patent: Jun. 29, 2010

(54) PROGNOSTIC INDICATORS OF CANINE LYMPHOID NEOPLASIA USING TUMOR-DERIVED PLASMA DNA

(75) Inventor: Laura J. Rush, Columbus, OH (US)

(73) Assignee: The Ohio State University, Columbus, OH (US)

( * ) Notice: Subject to any disclaimer, the term of this patent is extended or adjusted under 35 U.S.C. 154(b) by 25 days.

(21) Appl. No.: 11/998,155

(22) Filed: Nov. 28, 2007

Related U.S. Application Data

(60) Provisional application No. 60/861,501, filed on Nov. 28, 2006.

(51) Int. Cl.
*C07H 21/04* (2006.01)
*C12Q 1/68* (2006.01)

(52) U.S. Cl. .................. 435/6; 435/91.1; 435/91.2; 536/23.1; 536/24.3

(58) Field of Classification Search .................. None
See application file for complete search history.

(56) References Cited

OTHER PUBLICATIONS

Deligezer et al. (Clinica Chimica Acta, vol. 335, pp. 89-94, 2003).*
Lee et al. (Cancer, vol. 77, No. 9, pp. 1892-1898, 1996).*
Fournel-Fleury et al. (J. Comp. Path. vol. 117, pp. 35-59, 1997).*
Starkey et al. (Briefings in Functional Genomics and Proteomics, vol. 4, No. 2, pp. 112-128, Jul. 2005).*
Mulcahy et al. (Clinical Cancer Research, vol. 4, pp. 271-275, Feb. 1998).*
Oliver Gautschi, et al., Circulating Deoxyribonucleic Acid As Prognostic Marker in Non-Small-Cell Lung Cancer Patients Undergoing Chemotherapy, Journal of Clinical Oncology, vol. 22, No. 20, Oct. 15, 2004, pp. 4157-4164.
Ning Ren, et al., The Prognostic Value of Circulating Plasma DNA Level and Its Allelic Imbalance on Chromosome 8p In Patients With Hepatocellular Carcinoma, J Cancer Res Clin Oncol (2006) 132; pp. 399-407.
Sabine Jahr, et al., DNA Fragments in the Blood Plasma of Cancer Patients: Quantitations and Evidence for Their Origin From Apoptotic and Necrotic Cells, Cancer Research 61, pp. 1659-1665, Feb. 15, 2001.
Kyle D. Weaver, et al., Methylated Tumor-Specific DNA As a Plasma Biomarker in Patients With Glioma, Cancer Investigation 24:35-40, (2006).
Bret Taback, et al., Quantification of Circulatin DNA in the Plasma and Serum of Cancer Patients, Ann, N.Y. Acad. Sci. 1022: pp. 17-24 (2004).

Tsu-Lan Wu, et al., Cell-Free DNA: Measurement in Various Carcinomas and Establishment of Normal Reference Range, Clinica Chimica Acta 321 (2002), pp. 77-87.
Frank Diehl, et al., Detection and Quantification of Mutations in the Plasma of Patients With Colorectal Tumors, PNAS, Nov. 8, 2005, vol. 102, No. 45, pp. 16368-16373.
Hannes M. Muller, et al., Prognostic DNA Methylation Marker in Serum of Cancer Patients, Ann, N.Y. Acad. Sci. 1022: 44-49 (2004).
Andreas Widschwendter, et al., DNA Methylation in Serum and Tumors of Cervical Cancer Patients, Clinical Cancer Research, vol. 10, pp. 565-571, Jan. 15, 2004.
Gabriella Sozzi, et al., Analysis of Circulating Tumor DNA in Plasma At Diagnosis and During Follow-Up of Lung Cancer Patients, Cancer Research 61, pp. 4675-4678, Jun. 15, 2001.
N. Frickhofen et al., Rearranged Lg Heavy Chain DNA Detectable in Cell-Free Blood Samples of Patients With B-Cell Neoplasia, Blood, 1997, vol. 90, pp. 4953-4960.
Anthony T.C. Chan, et al., Plasma Epstein-Barr Virus DNA and Residual Disease After Radiotherapy for Undifferentiated Nasopharyngeal Carcinoma, Journal of the National Cancer Institute, vol. 94, pp. 1614-1619, No. 21, Nov. 6, 2002.
Anna Rogers, et al., Relative Increase in Leukemia-Specific DNA in Peripheral Blood Plasma From Patients Wtih Acute Myeloid Leukemia and Myelodysplasia, Blood, 2004, pp. 2799-2801.
M. Galeazzi et al., Dosage and Characterization of Circulating DNA: Present Usuage and Possible Applications in Systemic Autoimmune Disorders, Autoimmunity Reviews 2 (2003), pp. 50-55.
Dolores C. Garcia-Olmo et al., Detection of Circulating Tumor Cells and of Tumor DNA in Plasma During Tumor Progression in Rats, Cancer Letters 217 (2005), pp. 115-123.
Luis J. Herrera, et al., Quantitative Analysis of Circulating Plasma DNA As a Tumor Marker in Thoracic Malignancies, Clinical Chemistry 51:1, pp. 113-118 (2005).
Monika Jung, et al., Changes in Concentration of DNA in Serum and Plasma During Storage of Blood Samples, Clinical Chemistry 49, No. 6, 2003, pp. 1028-1029.
Victoria L. Singer, et al., Characterization of PicoGreen Reagent and Development of a Fluorescence-Based Solution Assay for Double-Stranded DNA Quantitation, Analytical Biochemistry 249, pp. 228-238 (1997).

(Continued)

*Primary Examiner*—Jeannie A Goldberg
(74) *Attorney, Agent, or Firm*—MacMillan, Sobanski & Todd, LLC

(57) ABSTRACT

A method of identifying an animal having a disease or condition without clinical symptoms includes detecting an elevated level of plasma DNA from blood or a blood fraction from the animal. In particular, the disease or condition can be a lymphoid neoplastic disease. Also, the plasma DNA can comprise a tumor-derived plasma DNA. In certain embodiments, the evaluation of the blood or blood fraction from the animal for the mutation assists in the identification of the disease or condition and/or its prognosis in the animal.

13 Claims, 6 Drawing Sheets

OTHER PUBLICATIONS

R.C. Burnett et al., Diagnosis of Canine Lymphoid Neoplasia Using Clonal Rearrangements of Antigen Receptor Genes, Veterinary Pathology, 40:32, pp. 32-41, (2003).

D. Schaefer et al., American Society for Veterinary Clinical Pathology (ASVCP) 40th Annual Meeting, Abstract #15, "Circulating Nucleic Acids As a Biomarker for Dogs With Cancer", Sep. 2005, p. 285.

D.M.W. Schaefer, et al., Quantification of Plasma DNA As a Prognostic Indicator in Canine Lymphoid Neoplasia, The Authors, Journal Compilation, Veterinary and Comparative Oncology, (2007), pp. 145-155.

Lana, Susan E. et al., Utility of Polymerase Chain Reaction for Analysis of Antigen Receptor Rearrangement in Staging and Predicting Prognosis in Dogs With Lymphoma, J. Vet Intern Med 2006, 20, pp. 329-334.

* cited by examiner

PROGNOSTIC INDICATORS OF CANINE LYMPHOID NEOPLASIA USING TUMOR-DERIVED PLASMA DNA

CROSS-REFERENCE TO RELATED APPLICATIONS

This application claims the benefit of U.S. Provisional Application No. 60/861,501, filed Nov. 28, 2006, the disclosure of which is incorporated herein by reference.

STATEMENT REGARDING FEDERALLY SPONSORED RESEARCH

This invention was not made with Government support and the Government has no rights in this invention.

TECHNICAL FIELD AND INDUSTRIAL APPLICABILITY OF THE INVENTION

There is provided herein a diagnostic and/or prognostic that includes measurement of circulating DNA in dogs that is useful to determine whether dogs with cancer have higher concentrations of plasma DNA than healthy dogs or dogs with non-malignant diseases. In a particular aspect, there is provided herein a diagnostic and/or prognostic indicator for lymphoid neoplasia.

BACKGROUND OF THE INVENTION

Domestic dogs were reported to have about 213 cases of cancer annually per 100,000 individuals in a survey performed several decades ago, which was similar to the incidence reported in humans at that time (approximately 300 per 100,000) (1). Although more recent studies of cancer incidence in dogs are not available, it is likely that the current incidence is even higher, as dogs are living much longer than they did decades ago. The development of spontaneous tumors in dogs more closely resembles tumorigenesis in humans than does experimentally induced cancer in rodent models, and as such, there is great interest in using dogs with cancer for translational research. Several recent clinical trials have validated the use of spontaneous canine tumors for the preclinical evaluation of novel therapeutics (2-4). Unfortunately, there are relatively few noninvasive methods to diagnose cancer and monitor therapy in veterinary medicine when compared to human medicine. Development of novel assays for these parameters would be useful for both initial evaluation of canine cancer patients as well as for following these patients non-invasively during the course of a clinical trial.

Measuring circulating plasma or serum DNA as a biomarker in humans with cancer has gained attention in recent years, but has not been investigated in veterinary species. Circulating cell-free DNA is detectable at low levels in the serum and plasma of healthy humans, and concentrations of circulating DNA are increased in many human cancer patients. This increase is seen in multiple tumor types, including hematopoietic tumors (e.g. lymphoma and leukemia), carcinomas (e.g. lung, breast, cervical, pancreatic and gastrointestinal tumors), and other tumor types such as Ewing's sarcoma, melanoma, and glioma (5-9). It has been reported that about 50% of all human cancer patients have increased circulating DNA (10). Furthermore, many of the same genetic and epigenetic changes are present in circulating DNA and in DNA from primary tumors, including mutations and/or aberrant promoter hypermethylation in p53, p16, and APC genes (8,11-21). These findings indicate that at least a portion of circulating DNA is derived from tumor cells. In humans, a portion of circulating DNA is derived from the primary tumors (11,14,16-18,21,39). It is noted, however, that circulating DNA also is increased in many non-lymphoid neoplasms in humans (5-10,12,19,20,43).

Circulating DNA in cancer has been explored in humans as a screening tool and a prognostic indicator, as well as for detection of residual disease after treatment. Two approaches for these analyses are either absolute quantification of circulating DNA or evaluation of specific molecular genetic defects (i.e. tumor-specific mutations or epigenetic changes) in the circulating DNA. Increased plasma DNA and/or genetic and epigenetic changes in plasma DNA have been associated with poor prognosis in a variety of tumor types (6,17,18). For example, mean plasma DNA levels in patients with lung cancer (even stage 1a disease) are higher than healthy controls, and increased DNA in pre-treatment plasma samples correlated with decreased survival in patients with non-small cell lung cancer (5,22). Plasma DNA concentrations also are increased in patients with both early and late stages of lymphoma, and circulating tumor-derived DNA was detected by PCR in 86% of patients with B cell leukemia or lymphoma (12,23). Persistence of circulating tumor DNA after initiation of treatment was associated with poor treatment response or early relapse in these patients (23).

In another study K-ras mutations were present in the plasma of 17 of 21 pancreatic cancer patients. Importantly, the mutation in plasma DNA was identified 5 to 14 months before clinical diagnosis in 4 patients with no evidence of neoplasia on initial biopsy but who had pancreatic carcinoma confirmed on later histopathology (15). Lastly, changes in circulating DNA correlate with the presence of residual disease after initiation of treatment (24,25). It is important to note, however, that increases in circulating DNA are not specific to cancer, and have been reported in inflammatory and autoimmune diseases, as well as other conditions (26-29). Exogenous DNA, including viral DNA and fetal DNA, also can be detected in circulation (24,30-32).

The phenomenon of circulating tumor DNA has rarely been explored in laboratory animals. Subcutaneous injection of cultured tumor cells into rats allowed detection of tumor-specific plasma DNA 3 weeks after inoculation (33). To our knowledge there have been no studies evaluating circulating DNA in spontaneous tumors of veterinary cancer patients.

SUMMARY OF THE INVENTION

In one aspect, there is provided a method of identifying an animal having a disease or condition without clinical symptoms by detecting an elevated level of plasma DNA from blood or a blood fraction from the animal. In a particular embodiment, the disease or condition is a lymphoid neoplastic disease. Also, the plasma DNA can comprise a tumor-derived plasma DNA. In certain embodiments, the evaluation of the blood or blood fraction from the animal for the mutation assists in the identification of the disease or condition and/or its prognosis in the animal.

Various objects and advantages of this invention will become apparent to those skilled in the art from the following detailed description of the preferred embodiment, when read in light of the accompanying drawings.

BRIEF DESCRIPTION OF THE DRAWINGS

FIG. 1A is a graph showing a histogram of plasma DNA from 40 healthy dogs, showing that the majority of dogs have 5 ng/ml of plasma DNA. FIG. 1B is a graph showing the median plasma DNA in healthy dogs divided into groups by age, sex, and breed. Error bars represent standard deviation. FIG. 1C is a graph showing a scatterplot of plasma DNA measurements in healthy dogs, dogs with non-neoplastic diseases, and various tumor types. *statistically significant (p<0.0001). F=female, FS=female spayed, M=male, MC=male castrated.

FIG. 2A is a graph showing Plasma DNA versus remission time. The majority of dogs had either plasma DNA >25 ng/ml and remission time <10 weeks (quadrant 1), or plasma DNA "25 ng/ml and remission time >10 weeks (quadrant 4). FIG. 2B is a graph showing a Kaplan-Meier plot for remission time using 15 ng/ml as a cutoff showed no statistically significant difference (n=20, p=0.1997). FIG. 2C is a graph showing a Kaplan-Meier plot using 25 ng/ml as a cutoff showed a difference that was statistically significant (n=20, p=0.0076). FIG. 2D is a graph showing the same as FIG. 2C, except considering only those dogs in clinical substage b (n=12, p=0.0442).

FIG. 3A shows PARR on plasma from a healthy dog and shows a band only in the positive control lane (Cµ). FIGS. 3B and 3C show PARR on DNA from tumor (FIG. 3B) and plasma (FIG. 3C) from a patient with lymphoma show the same oligoclonal bands in both, indicating that at least a portion of the plasma DNA is tumor-derived. Lane markers: Cµ (positive control primers), IgH-M and IgH-m (IgH major and IgH minor B cell receptor), TCR (T cell receptor).

DETAILED DESCRIPTION OF THE PREFERRED EMBODIMENT(S)

Figure 1A:
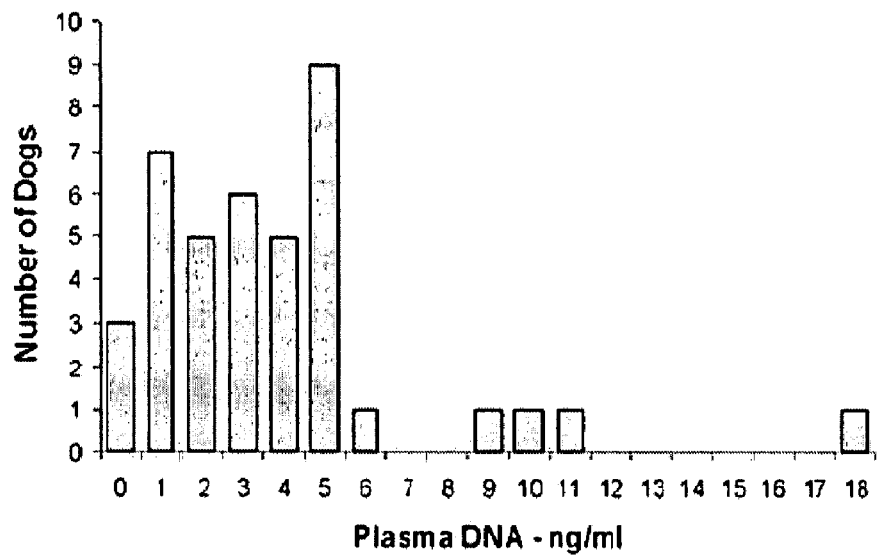
FIGS. 1A, 1B and 1C are a summary of plasma DNA concentrations in healthy dogs and dogs with neoplastic and non-neoplastic diseases.

In one aspect, there is proved a method to test for the presence of circulating DNA in domestic animals with cancer. In a particular aspect, the method includes a method for evaluating animals with cancer that have higher concentrations of circulating DNA than healthy animals or animals with non-neoplastic diseases. The method provides a clinically useful ancillary test for diagnosis or prognosis of canine cancer. It is to be understood, that while one specific embodiment described herein is directed in particular to canines, it is within the contemplated scope of the methods described herein that such methods are useful with other animals, including domesticated and undomesticated animals.

In another aspect, this invention relates to the discovery that both non-particle and particle associated nucleic acids are present in blood plasma in canines and can be used to evaluate disease conditions. In particular, there is described herein new methods of simply and accurately evaluating disease conditions in animals are that needed in order to aid in the detection, prognosis, diagnosis, monitoring and treatment of disease in animals worldwide.

In a particular aspect, there is provided a method for evaluating a disease condition in an animal suspected of suffering or known to suffer from the disease condition. The method includes obtaining a blood sample from the animal suspected of suffering or known to suffer from a disease condition, isolating plasma from the blood sample, separating the plasma into two or more fractions containing different relative concentrations of particle-associated and non-particle associated nucleic acid, and evaluating the disease condition by determining the amount or concentration or characteristic of nucleic acid in one or more fractions and comparing the amount or concentration or characteristic of nucleic acid in one or more fractions to a control.

In certain embodiments, the nucleic acid is plasma DNA, and in particular, a tumor-specific DNA. The method can further include the step of amplifying the nucleic acid.

It is within the contemplated scope of the embodiments described herein that the nucleic acid can be amplified by PCR or reverse-transcriptase PCR, including where the nucleic acid is amplified by real-time PCR or real-time reverse-transcriptase PCR. In certain embodiments, the fractions are separated by filtration, centrifugation or ultracentrifugation.

The method of evaluating a disease or physiologic condition in the animal aids in the detection, monitoring, prognosis or treatment of the animal.

In another aspect, there is provided a method for evaluating the disease condition of an animal suspected of having, known to have, or at risk of having, a lymphoid neoplasia-related disease. In another aspect, the method includes detecting cancer where an elevation thereof is indicative of cancer in the subject. In still another aspect, there is provided a method for staging cancer where an elevation thereof is indicative of an advanced stage of the cancer in the subject.

In still another aspect, there is provided a method of prognosing cancer that includes providing a plasma sample from an animal; and detecting an elevated level of one or more plasma nucleic acids in the sample. An elevation thereof is indicative of a poor prognosis of the cancer in the animal.

In yet another aspect, there is provided a packaged product that can include a container; one or more agents for detecting one or more nucleic acids in a sample of animal plasma; and an insert associated with the container and indicating that the sample contains an elevated level of the plasma nucleic acid in the sample.

Also, there is provided a kit that can include one or more agents for detecting one or more DNA markers in a sample comprising animal plasma.

In a particular aspect, there is provided a method for determining a prognosis in an animal with a lymphoid neoplasia-related disease. The method generally includes the steps of: (i) purifying extracellular nucleic acid from blood or a blood fraction from an animal to prepare extracted extracellular nucleic acid; and concurrently or sequentially; (ii) amplifying extracellular nucleic acid or a fragment thereof, or amplifying a signal from the extracellular nucleic acid or a fragment thereof; and, (iii) detecting the product of the amplified extracellular nucleic acid or the product of its amplified fragment, or the amplified signal of the extracellular nucleic acid or the amplified signal of a fragment thereof. The detection determines the prognosis for the lymphoid neoplasia in the animal. The extracellular nucleic acid can be a DNA encoding a mutated gene or fragment thereof.

Also, the method can include a step where extracellular nucleic acid is purified from the plasma fraction of blood. In certain embodiments, the nucleic acid encodes a mutated oncogene or fragment thereof. Examples include where the mutated oncogene is a mutated K-ras, p53 or Rb.

It is within the contemplated scope of practicing the method described herein that the product of the amplified mutated gene DNA is detected using a detection method that includes gel electrophoresis, single strand conformation polymorphism, heteroduplex analysis, denaturing gradient gel electrophoresis, mismatch cleavage assay, immunological detection methods, nucleic acid hybridization, Southern blot analysis, electrochemiluminescence, reverse dot blot detection, or high-performance liquid chromatography.

In certain embodiments, the method optionally further includes enriching the extracted extracellular nucleic acid or a fragment thereof, wherein the nucleic acid or a fragment thereof is concentrated or isolated from the remaining extracted extracellular nucleic acid. The enriched mutated gene DNA or a fragment thereof can be amplified using an amplification method that is polymerase chain reaction, ligase chain reaction, boomerang DNA amplification, Q-beta replication, transcription-based amplification, isothermal nucleic acid sequence based amplification, self-sustained sequence replication assay, strand displacement activation, or cycling probe technology. Also, the mutated gene DNA or a fragment thereof can be enriched through an endonuclease-mediated restriction digestion, or by hybridization of the mutated gene DNA or a fragment thereof to an oligonucleotide to form a hybridized complex.

Disclosed herein is the discovery that circulating nucleic acids in the plasma or serum of canines are associated with certain disease conditions. Until the present discovery, little had been known about the characteristics and biological origin of circulating nucleic acids in animals, and in canines, in particular. Without being bound by theory, as cells undergoing apoptosis dispose nucleic acids into apoptotic bodies, it is believed that at least part of the circulating nucleic acids in at least the plasma of animal subjects is particle associated. In this application, it is demonstrated for the first time that circulating nucleic acids exist in both particle and non-particle associated form in the plasma of animal subjects can be used to evaluate the prognosis of such animals suffering from a lymphoid neoplastic related disease.

It is also demonstrated that by separating the circulating nucleic acids present in the plasma of animal subjects into their particle associated and non-particle associated forms, disease conditions can be simply and accurately evaluated.

The phrase "evaluating a disease condition" refers to assessing the disease condition of an animal. For example, evaluating the condition of an animal can include detecting the presence or absence of the disease in the animal. Once the presence of disease in the animal is detected, evaluating the disease condition of the animal may include determining the severity of disease in the animal. It may further include using that determination to make a disease prognosis, e.g. a life-span prediction or treatment plan. Evaluating the condition of an animal may also include detecting that an animal no longer has a disease condition but has suffered from the disease condition in the past. Evaluating the disease condition in that instant might also include determining the probability of reoccurrence of the disease condition or monitoring the reoccurrence in an animal. Evaluating the disease condition might also include monitoring an animal for signs of disease. Evaluating a disease condition therefore includes detecting, diagnosing, or monitoring a disease condition in an animal as well as determining a prognosis or treatment plan. The method of evaluating a disease condition aids in risk stratification.

As used herein the term "blood plasma" may generally refer to the fraction of whole blood resulting from centrifugation of blood treated with anticoagulants. Also as used herein, the phrase "comparing the amount or concentration or characteristic of nucleic acid in one or more fractions to a control" can be considered to be equivalent to comparing the amount or concentration or characteristic of nucleic acid in one or more fractions to a standard. The phrase "comparing the amount or concentration or characteristic of nucleic acid in one or more fractions to a control" may also include making an inter-fraction comparison.

Circulating nucleic acids exist in the blood plasma of both healthy animals and diseased animals in both particle-associated and non-particle associated forms. By comparing the relative concentration of particle-associated and non-particle associated nucleic acid in an animal suspected of having a disease, known to have a disease or at risk of having a disease to the relative concentration of particle-associated and non-particle associated nucleic acid in a healthy animal, in a sample taken from the animal at an earlier time, or in a sample taken from another diseased animal, it is possible to evaluate disease conditions. By making inter-fraction comparisons, it is also possible to evaluate disease conditions. In some embodiments, the control might not be a second sample but instead an average of data from a variety of animal who are classified as healthy or as suffering from various disease conditions, e.g., cancer. The data collected may correspond to various levels or concentrations of non-particle associated nucleic acid in the blood to severity, prognosis or diagnosis of disease. For example, using the methods described herein, a skilled practitioner can compare the amount or concentration of non-particle associated nucleic acid in a first fraction of an animal to a control and determine the presence or absence of disease in the animal from which the sample was obtained. The skilled practitioner can also use the comparison to determine disease type or stage. The skilled practitioner might also use the comparison to determine disease severity or predict patient life-span. The skilled practitioner can use the comparison to aid in risk stratification, monitoring or treatment of the disease condition in an animal.

Circulating nucleic acid present in the blood plasma may exist in two forms, "particle-associated" and "non-particle associated". Particle-associated nucleic acids may be defined as nucleic acids that are contained inside or adhered to or linked to or on the surface of particles. The term "particle" may be defined as any material that can be demonstrated by physical means; for example, the particle can have a finite size from 0.1 µm to 5 µm in diameter or one that is pelletable by ultracentrifugation following prior filtration using a 5 µm filter. Also, for example, in certain embodiments, sizes larger than 5 µm in diameter can include intact cells and so may be excluded. Physical means used to determine the size of particle-associated nucleic acids include, but are not limited to, centrifugation, ultracentrifugation, sedimentation, filtration, optical microscopy or electron microscopy. Accordingly, the term "particle-associated nucleic acids" includes both extracellular and intracellular nucleic acids present in the blood plasma providing that the nucleic acids are bound to a particle or one which is pelletable by ultracentrifugation. For example, extracellular nucleic acids may be complexed to ribosomes, lipids or proteolipids. They may be protein-bound or within apoptotic bodies. The term "particle associated nucleic acids" may also include those extracellular nucleic acids complexed to ribosomes, lipids or proteolipids.

"Nucleic acid" refers to a deoxyribonucleotide or ribonucleotide polymer in either single- or double-stranded form, and unless otherwise limited, would encompass known analogs of natural nucleotides that can function in a similar manner as naturally occurring nucleotides. The phrase "a sample of blood plasma", as used herein, refers to a sample of blood plasma obtained from an animal subject. Frequently the sample will be a "clinical sample" which is a sample derived from an animal with a disease or suspected of having a disease or a physiological condition needing medical attention. The sample as initially obtained from the animal may contain additional components other than blood plasma. For example, the sample may initially be a sample of whole blood purified to its plasma components. Either "fresh" blood plasma, or frozen (stored) and subsequently thawed plasma may be used for the methods described herein.

Materials and Methods

Selection of dogs. All procedures were approved by the Institutional Laboratory Animal Care and Use Committee (ILACUC). Blood was collected from 40 healthy dogs (12 weeks to 12 years old) who were either presented for routine wellness examinations at The Ohio State University Veterinary Teaching Hospital (OSUVTH) or were owned by employees of the veterinary college who volunteered to participate in the study. Dogs with cancer (n=80; 2-12 years old) and non-neoplastic diseases (n=20; 2-12 years old) were presented to either the OSUVTH or to MedVet Associates, a private veterinary referral hospital. Each group had approximately 50% females and males, with the majority being spayed or neutered. Sixty-five to 85% of the dogs in the 3 groups were purebred, with the remainder being mixed breed. All cancer diagnoses were confirmed either by histopathology or cytopathology, and none of the dogs with cancer received any treatment prior to blood collection. Remission times were calculated from the beginning of treatment.

Sample collection and processing. Initial experiments were performed using both plasma and serum. Serum results had a higher standard deviation (data not shown), so plasma was used for the remainder of the study. Two to 4 ml of blood in ethylenediamine tetraacetic acid (EDTA) was collected from each patient. Following centrifugation at 1500 g for 10 minutes, plasma was transferred to a 1.5 ml microcentrifuge tube and centrifuged a second time at 1000 g for 5 minutes to remove residual blood cells that could falsely increase plasma DNA measurements (5,6,34). The top portion of the plasma was transferred to a second 1.5 ml microcentrifuge tube and stored at −20° C. All samples were processed within 2 hours of collection to avoid in vitro lysis of white blood cells and subsequent release of DNA (35).

DNA purification from plasma and serum. DNA was isolated from 204.1 of plasma or serum using QIAamp DNA Mini Kit (QIAGEN Inc., Valencia, Calif.) according to the manufacturer's instructions using the blood and body fluid spin protocol. DNA was isolated within one month of collection, and samples were stored at −20° C.

Quantification of plasma and serum DNA. Circulating DNA was measured using PicoGreen® reagent (Invitrogen Corporation, Carlsbad, Calif.) according to the manufacturer's protocol. PicoGreen is a cyanine dye that is nonfluorescent when unbound, but fluoresces proportionate to the amount of double-stranded DNA bound by the dye (36). A standard curve was created by serial dilution of lambda DNA to make seven levels of standards, 500, 250, 100, 50, 10, 5, and 1 ng/ml. The PicoGreen® working reagent was combined with either lambda DNA or purified patient plasma DNA in each well of a 96-well plate (Corning Costar 3631, Corning, N.Y.). All standards and patient samples were measured in triplicate. Relative fluorescent units (RFU) were measured using an FLx800 microplate fluorescence reader with KCjunior software (BioTek Instruments, Inc., Winooski, Vt.) set at excitation/emission 485/528. The average RFU of 3 blank wells (containing only PicoGreen®reagent and Tris-EDTA) was subtracted from the average RFU of each sample or standard. The RFU of the standards was plotted against ng/ml of DNA to obtain a standard curve, and the regression equation was used to convert RFU to ng/ml of DNA for each sample.

Assay validation. The linear range of the assay was evaluated by measuring serial dilutions of lambda DNA ranging from 0.1-2000 ng/ml. Each dilution was measured at least 6 times on different days and an average of the measured values was used to assess linearity by least squares regression. For measurement of within-run variation, plasma DNA levels from 5 different patient samples were measured 8-11 times each on the same 96-well plate. For measurement of between-run variation, plasma DNA levels from 6 different patient samples were measured 4-7 times, with each measurement taken on a different day.

PCR for assessment of plasma DNA clonality. The clonality of the T cell receptor gamma (TCRγ) gene or immunoglobulin heavy chain (IgH) gene rearrangements was compared between plasma DNA and tumor-derived DNA. Tumor cells from fine needle aspirates were scraped from a dried microscope slide into a microcentrifuge tube and mixed with 280 μl of 1×PBS. DNA was then isolated with the QIAamp DNA Mini Kit (QIAGEN) using the same protocol as for plasma DNA. DNA from formalin-fixed tumor samples was isolated from paraffin blocks (4-5 sections from each block, each section 10 μm thick). The paraffin was dissolved with xylene, and DNA was purified with QIAamp DNA Mini Kit according to the manufacturer's instructions using the tissue protocol. PCR for antigen receptor rearrangement (PARR) was performed as previously described (37). Four sets of primers are used for canine antigen receptor genes. Cμ primers serve as a positive control to confirm the presence of amplifiable DNA and should amplify a 130 bp fragment in all samples. Two sets of primers are used to amplify the IgH gene, and one set of primers amplifies the TCRγ gene. PCR products were electrophoresed on an 8% polyacrylamide gel at 250 volts for 75 minutes and stained with ethidium bromide.

Statistical Analysis. Statistical analysis was performed using SAS version 9.1 software (SAS Institute Inc., Cary, N.C.). In each dog group, summary statistics (mean, median, standard deviation, minimum and maximum values) were calculated for the entire group, as well as for each age group, sex group, and breed group within the healthy dogs. The nonparametric Kruskal-Wallis or Wilcoxon rank sum test was then performed to test for significant group differences. Plasma DNA summary statistics were calculated for the healthy, non-cancer, and cancer groups. Pairwise Wilcox on rank sum tests were performed to assess group differences. The cancer group was then divided into subgroups based on tumor type (lymphoid neoplasia, carcinoma, sarcoma, and other types) and plasma DNA concentrations from each tumor type were compared to the healthy dog group. Due to the large differences in variability between the different groups as well as the skewness of the data, the data were log-transformed, and analysis of variance (ANOVA) was used to determine if significant differences in plasma DNA existed between the healthy group and all other groups. Nonparametric tests were used to determine differences in plasma DNA levels with various clinicopathologic data among dogs with lymphoid neoplasia (presence of symptoms at diagnosis, histologic grade, and immunophenotype). Kaplan-Meier plots for remission times were produced for plasma DNA cutoff points of >15 ng/ml and >25 ng/ml. A p value of <0.05 was interpreted to be significant.

Results

Assay validation. Linearity of the PicoGreen® assay was assessed by repeated measurement of serial dilution of lambda DNA ranging from 0.1 to 2000 ng/ml. Regression analysis revealed the best linearity to be 1 to 500 ng/ml (slope 1.0261, y-intercept −0.1376, and standard error 2.08) (data not shown).

Precision was analyzed by determining coefficients of variation (CV) within the same run and between runs on several samples with high, moderate, and low plasma DNA. For within-run variation, CV ranged from 20.5%-1.3% in samples with means ranging from 4-90 ng/ml respectively (average 7.9%). For between-run variation, CV ranged from 27.2%-7.0% in samples with means ranging from 5-171 ng/ml (average 15.6%).

Figure 1B:
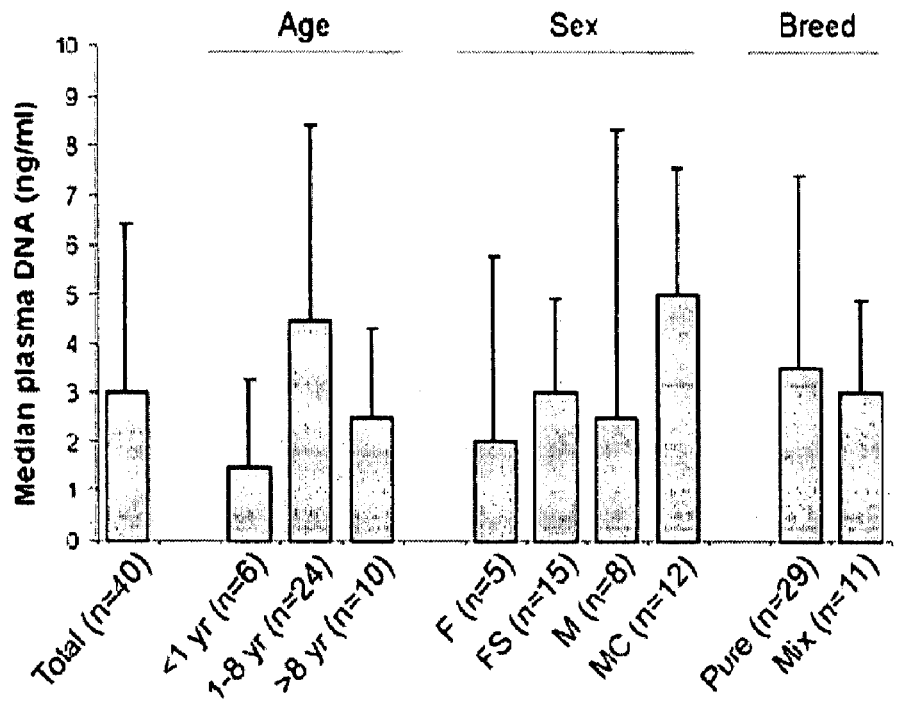

Quantification of plasma DNA from healthy dogs. To determine if dogs with cancer have high levels of circulating DNA, plasma DNA levels in healthy dogs was evaluated. Plasma DNA was quantified from 40 dogs ranging in age from 12 weeks to 12 years old, with both sexes and multiple breeds represented. Mean and median plasma DNA concentrations were 4 ng/ml and 3 ng/ml respectively (standard deviation=3.3). All 40 healthy dogs had values "18 ng/ml (FIG. 1A), and the reference interval was determined to be 115 ng/ml using the central 95 percent (38). Results were then stratified by age, sex, and breed. Three age groups were chosen to represent young (<1 year old, n=6), adult (1-8 years, n=24), and older (>8 years, n=10) dogs. There was not a large enough sample size from any one breed to determine differences between breeds, so all purebred dogs were combined in one group. Dogs less than 1 year of age had slightly lower plasma DNA than the 1 to 8 year old dogs, which was marginally significant (p=0.0463). No other age, sex, or breed differences were statistically significant (FIG. 1B).

Figure 1C:
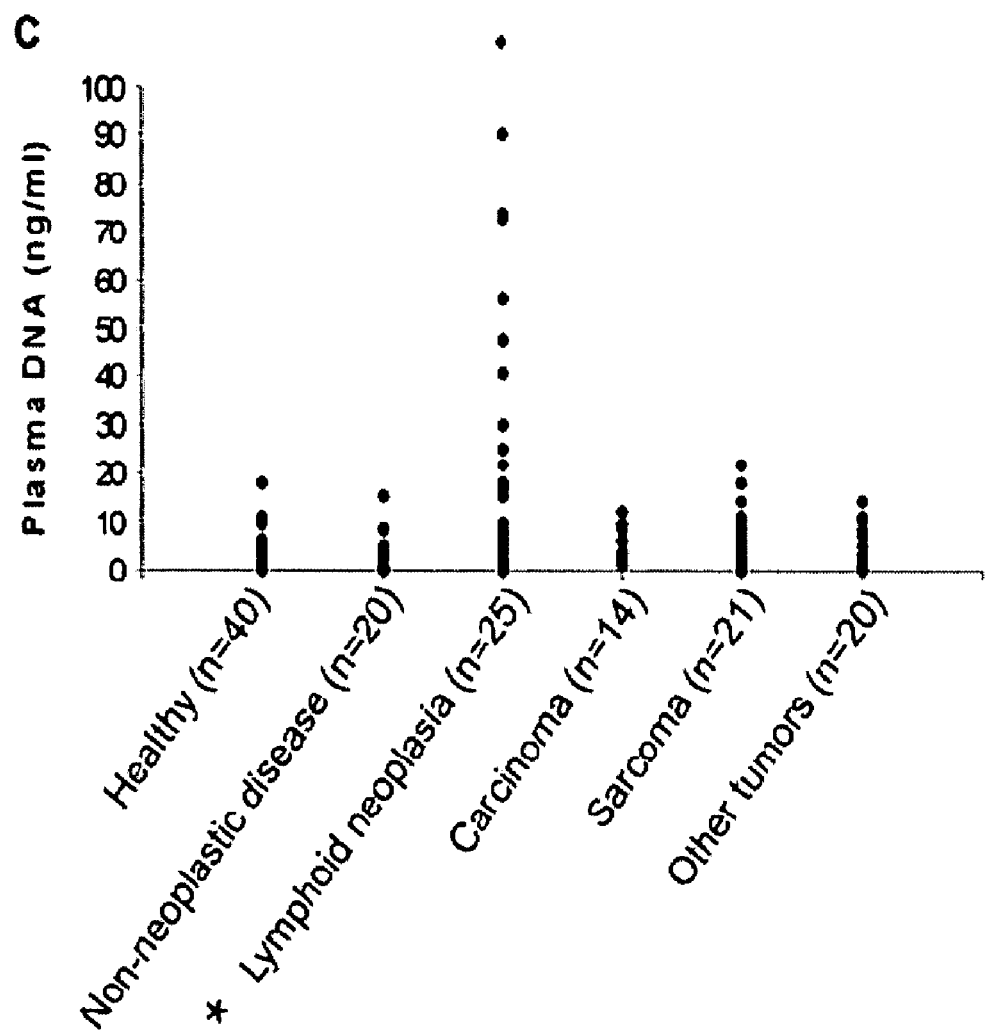

Quantification of plasma DNA from dogs with cancer and non-neoplastic diseases. These tests showed that dogs with cancer have higher concentrations of circulating DNA than healthy dogs or dogs with non-neoplastic diseases. Plasma DNA was quantified from 80 dogs with cancer (including lymphoid neoplasias, carcinomas, sarcomas, and other tumor types such as mast cell tumor and melanoma) and 20 dogs with non-neoplastic diseases (including various immune-mediated, infectious, inflammatory, endocrine, and other diseases). A scatterplot of values for each group is shown in FIG. 1C.

Twelve of 25 (48%) dogs with lymphoid neoplasia (lymphoma and lymphocytic leukemia) had plasma DNA higher than the reference interval. Most of the values ranged from 0 to 91 ng/ml (n=24), except for one dog with lymphoma that had a plasma DNA measurement of 1019 ng/ml. After log-transformation of the data and analysis of variance (ANOVA), we determined that the lymphoid neoplasia group had significantly higher plasma DNA than the healthy group (p<0.0001), with plasma DNA close to four fold higher than the healthy dog group (3.93 fold difference, 95% confidence interval 2.1-7.36). Sensitivity and specificity of plasma DNA >15 ng/ml for the diagnosis of lymphoid neoplasia were 0.480 (95% CI 0.300-0.665) and 0.952 (95% CI 0.869-0.981), respectively. The other cancer groups and the non-neoplastic group had circulating DNA values similar to the healthy dogs, with only three dogs having mildly increased plasma DNA (2 dogs with hemangiosarcoma and 1 dog with osteosarcoma, plasma DNA range 18 to 22 ng/ml).

| Clinicopathologic correlation in dogs with lymphoid neoplasia. Malignancies (n = 25) | |
|---|---|
| Age Range | 4.5 to 14 years |
| Gender | 12 female and 13 male |
| Diagnosis | Lymphoma, 22 |
| | Acute lymphocytic leukemia, 2 |
| | Chronic lymphocytic leukemia, 1 |
| Site of involvement | Peripheral lymph nodes, 11 |
| | Multicentric, 7 |
| | Other (only GI, bone marrow, spleen, or liver), 7 |
| Immunophenotype | B cell, 12 |
| | T cell, 4 |
| | Not available, 9 |
| Clinical substage* | Substage a (asymptomatic), 8 |
| | Substage b (symptomatic), 17 |

*Dogs were categorized as substage b if they exhibited lethargy, inappetence, weight loss, vomiting, diarrhea, polyuria, or polydypsia.

Dogs with systemic illness (clinical substage b) had significantly higher plasma DNA values than dogs without systemic illness (substage a) (p=0.0092). No other significant differences were noted.

Twenty of the 25 dogs with lymphoid neoplasia were treated with similar multi-drug chemotherapy protocols. We compared plasma DNA concentrations to remission times in these 20 dogs to determine the prognostic significance of increased plasma DNA (FIG. 2A).

Figure 2A:
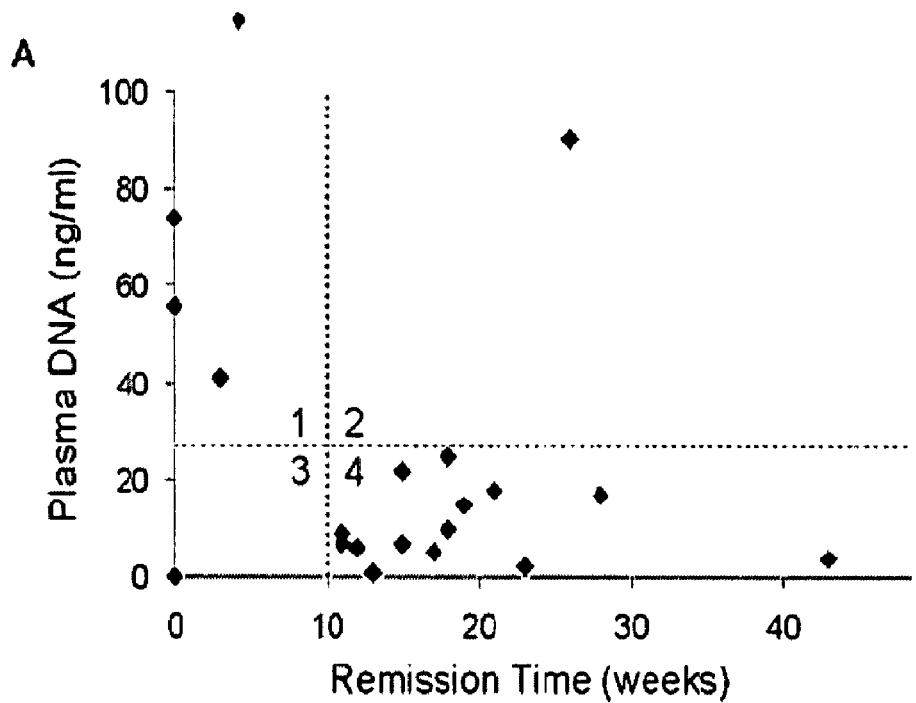
FIGS. 2A, 2B, 2C and 2D show plasma DNA versus remission time in dogs with lymphoid neoplasia treated with multidrug chemotherapy.

The majority of the dogs segregated into two groups: those with "25 ng/ml of plasma DNA and remission times >10 weeks (FIG. 2A, area 4), and those with >25 ng/ml of plasma DNA and remission times <5 weeks (FIG. 2A, area 1). This suggests that 25 ng/ml of plasma DNA is a useful clinical cutoff for prognostic indication in these patients.

Figure 2B:
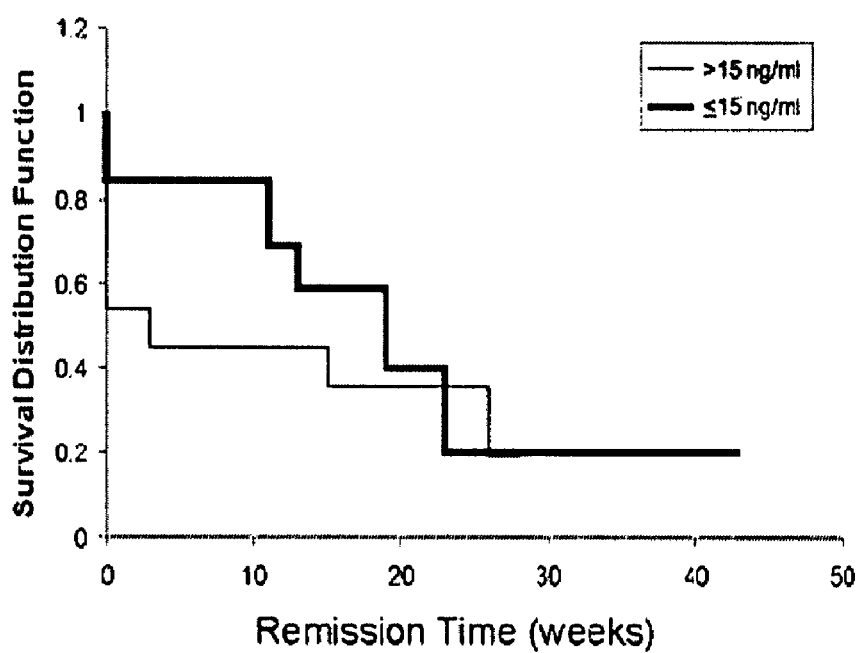
Figure 2C:
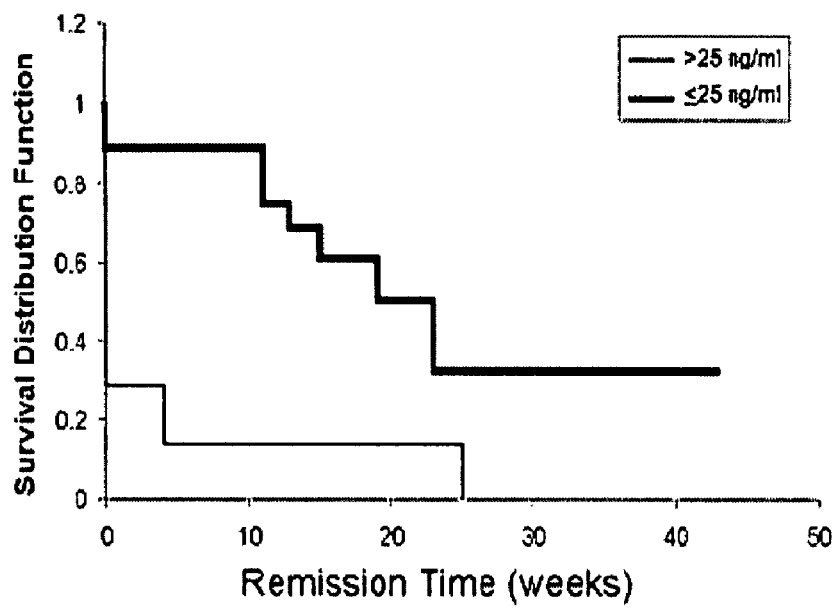

For dogs with lymphoid neoplasms, Kaplan-Meier plots depicting remission times were created using both the reference interval cutoff of 15 ng/ml and the clinical cutoff of 25 ng/ml (FIGS. 2B and 2C).

Remission times for dogs above and below 15 ng/ml were not statistically different (p=0.1997). However, when the 25 ng/ml cutoff was applied, those with high plasma DNA had significantly shorter remission times (p=0.0076). Nonparametric tests demonstrated no significant differences based on immunophenotype or histological grade (p=0.9267 and p=0.1329, respectively). However, those patients with substage b (clinically ill at the time of diagnosis) had significantly higher plasma DNA than those with substage a (p=0.0092).

Figure 2D:
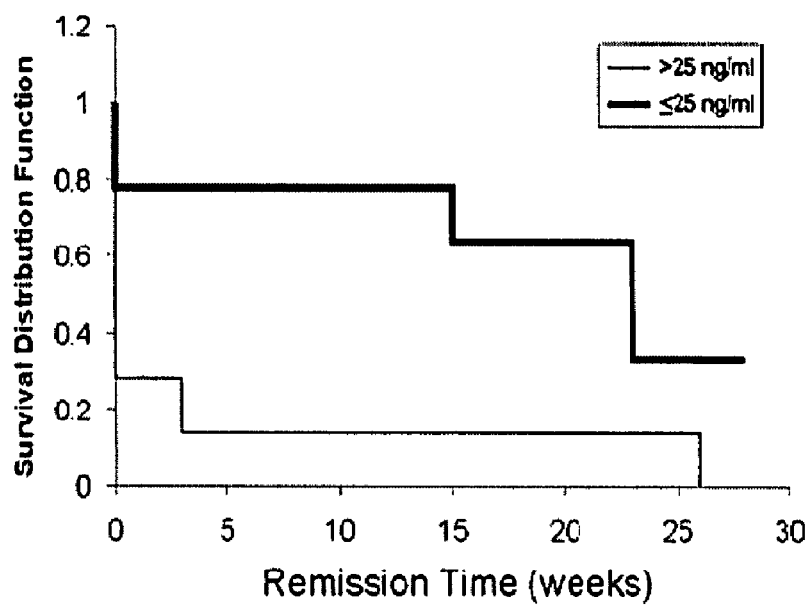

Remission times were then compared among only those dogs with substage b (n=12) disease to determine whether increased plasma DNA has prognostic significance simply because those dogs are more severely ill. A Kaplan-Meier plot using 25 ng/ml as the cutoff revealed that those with low plasma DNA responded better to treatment even when dogs that were not clinically ill were removed from the sample (FIG. 2D). This difference was marginally significant (p=0.0442).

| PCR for assessment of plasma DNA clonality. In lymphoid malignancies, DNA from dogs with lymphoma | | | |
|---|---|---|---|
| Sample Number | Plasma DNA concentration (ng/ml) | PARR on plasma DNA* | PARR on tumor DNA* |
| 1 | 1019 | + | + |
| 2 | 48 | + | + |
| 3 | 9 | − | + |
| 4 | 2 | + | + |
| 5 | 73 | + | N/A |
| 6 | 2 | + | N/A |
| 7 | 18 | + | N/A |
| 8 | 17 | − | N/A |
| 9 | 15 | + | N/A |

*"+" indicates presence of clonal band, "−" indicates lack of clonal band, N/A indicates that tumor DNA was not available.

Figure 3A:
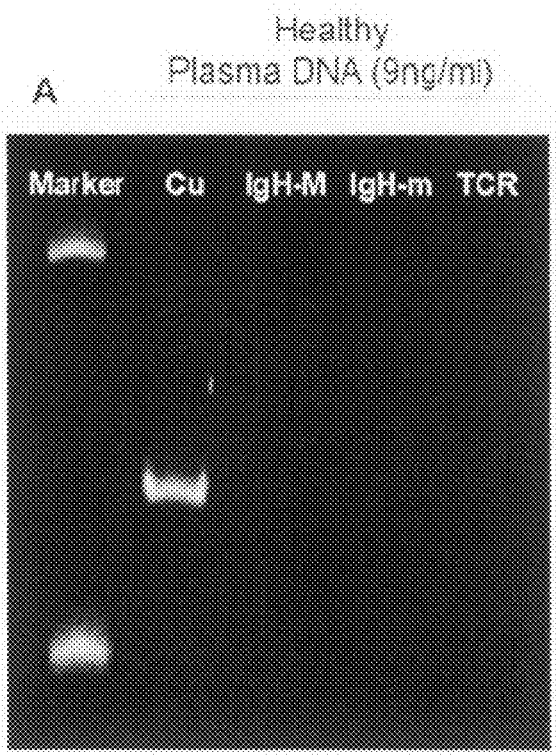
FIGS. 3A, 3B and 3C show the PCR for antigen receptor rearrangement (PARR) from plasma and tumor DNA.
Figure 3B:
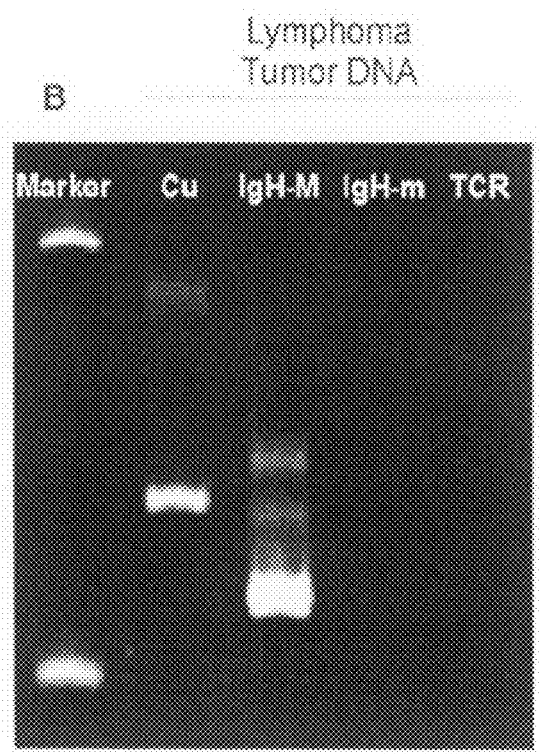
Figure 3C:
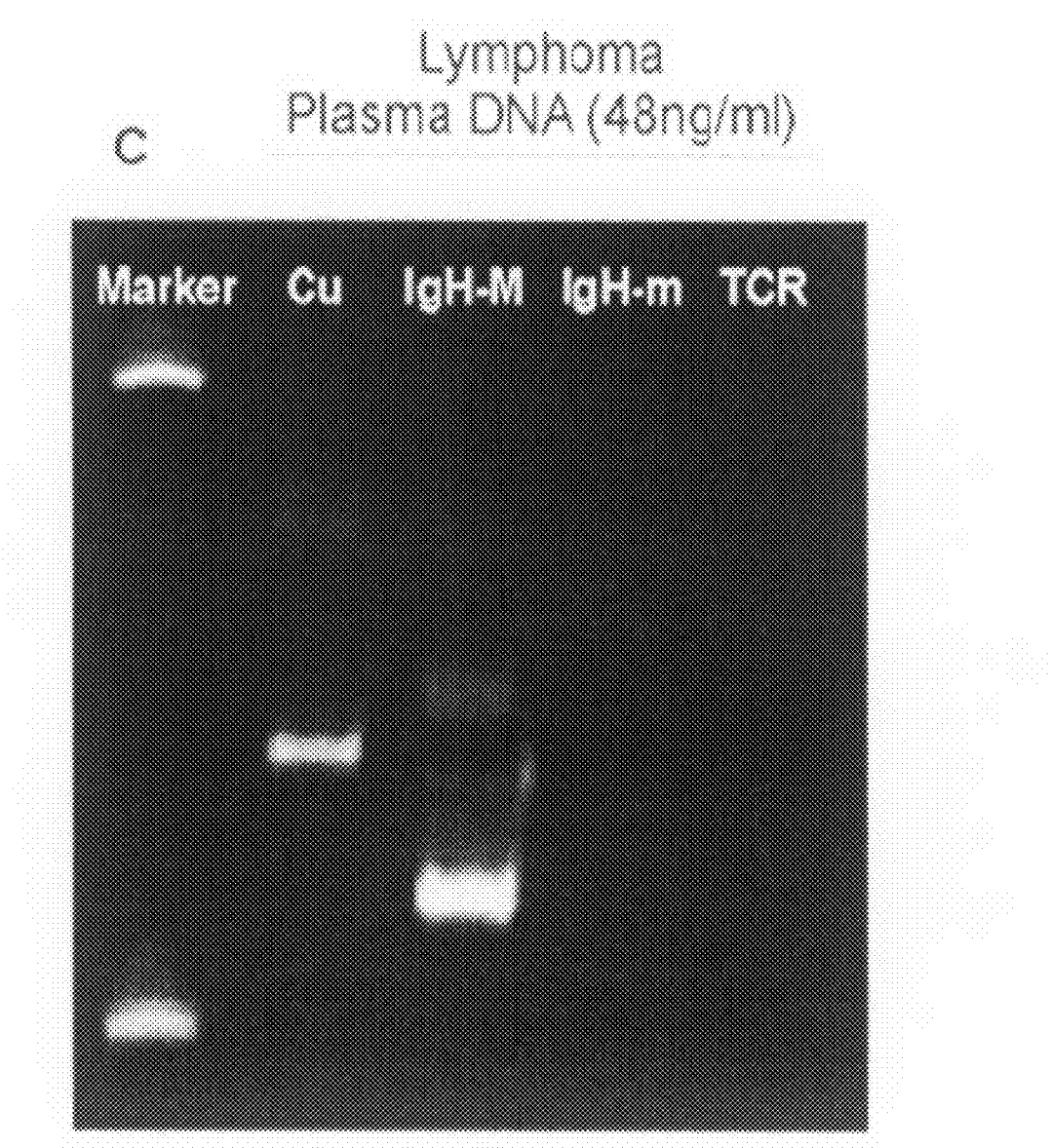

A negative PARR on plasma from a healthy dog is shown in FIG. 3A, along with a representative result using plasma and tumor DNA from a dog with lymphoma (FIGS. 3B and 3C).

Five additional dogs with lymphoma had adequate plasma sample volume to perform PARR on circulating DNA, but material from the primary tumor was unavailable. Four of these dogs had clonal products visible. Altogether, seven out of 9 lymphoma patients (78%) were positive for clonal antigen receptor DNA in the plasma (summarized in Table 2).

Discussion

The clinical utility of quantifying circulating DNA in dogs with cancer was assessed. Cancer is frequently diagnosed in the canine population, and affected dogs would greatly benefit from strategies to enhance earlier diagnosis, improve risk stratification and assist in determination of prognosis.

The method described herein allows reliable detection of low levels of DNA in plasma, with linearity down to 1 ng/ml. PicoGreen® reagent was used instead of real time PCR because a fluorescence assay has better potential than real time PCR for conversion to a test that can be performed in-house in veterinary hospitals. An alternative method for quantification of circulating DNA is real time PCR.

Plasma DNA concentrations were measured in 40 healthy dogs to establish a reference interval for our assay. The reference range was 1-15 ng/ml as calculated by the central 95%, which is similar to results in human studies using double-centrifuged plasma samples.

When healthy dogs were stratified by age, sex, and breed, the only difference noted was a marginally significant decrease in plasma DNA in the young dog group (<1 year old, n=6), which may be due to the small sample size. When serum DNA levels from healthy humans were separated by age and sex, there was no gender difference noted, similar to the studied dogs, but younger (<20 years, n=25) and older patients (>60 years, n=25) had slightly higher serum DNA. However, the difference in the studied dog age groups and these human age groups are small and should not affect clinical interpretation.

In one aspect, there is provided herein an evaluation of circulating DNA levels in dogs with cancer and non-neoplastic diseases. Plasma DNA was measured in 20 dogs with non-neoplastic diseases and in 80 dogs with various cancers, and the only group with a significant increase was the group with lymphoid neoplasia (lymphoma and lymphocytic leukemia). Twelve of 25 (48%) of these dogs had plasma DNA higher than the reference interval. In addition, there were three dogs with other tumor types that had mild increases in plasma DNA: two dogs with hemangiosarcoma and one dog with osteosarcoma (plasma DNA 1822 ng/ml). The analytical specificity for increased plasma DNA with lymphoid neoplasia is fairly high (0.952), but the sensitivity is low (0.480).

There is also provided herein a method for screening, using high plasma DNA as a screening test, for lymphoma, and in particular for screening specific breeds at high risk of developing this neoplasm (40-42).

Increased circulating DNA does appear to have prognostic significance. Dogs with lymphoid neoplasia that had plasma DNA >25 ng/ml had shorter remission times regardless of clinical substage. In certain embodiments, the use of a 25 ng/ml cutoff can be used; however, in other embodiments, the cutoff can be different. No significant differences in plasma DNA levels were noted based on immunophenotype or histological grade.

The reason for the restriction of increased plasma DNA to dogs with lymphoid neoplasia is unclear. Dogs with multicentric lymphoma may have a higher tumor burden than dogs with other tumors. Complete staging of disease was not performed and comparisons of tumor burden were not performed. It is hypothesized that the reason for increased plasma DNA being mainly restricted to lymphoid neoplasia is related to cell viability. Necrosis, apoptosis, and cell fragility are frequently encountered in specimens collected from lymphoid neoplasms (44,45). This propensity for cell disruption may allow increased leakage of tumor DNA into circulation; however, the amount of necrosis and apoptosis among different tumor types was not compared.

PCR to detect clonal lymphoid DNA showed that a portion of the circulating DNA in the dogs is tumor-derived. The examples herein show that the same clonal DNA was present in the plasma and primary tumor. PARR on plasma from seven of nine dogs (78%) had a clonal band identified.

Using this same PARR method in dogs with lymphoma, with DNA isolated directly from whole blood rather than plasma or serum, one group demonstrated clonal lymphoid DNA in 73% of dogs with lymphoma (46). However, that finding did not have prognostic significance for disease-free interval or survival. While direct comparison between the present method described herein and the present study cannot be made due to the different sample types, it is now believed that the quantity of circulating DNA may have more significance that merely the presence or absence of circulating tumor DNA.

In another aspect, there is provided a method for evaluating tumor-specific molecular changes in circulating DNA such as detection or quantification of specific gene mutations or epigenetic changes. This allows more specific evaluation of circulating tumor DNA rather than circulating DNA from other cells such as inflammatory cells. The method described herein is also useful for the diagnosis, prognosis, and detection of residual disease. In certain aspects, evaluation of the presence and diagnostic or prognostic value of circulating tumor DNA in non-lymphoid tumors can be accomplished by evaluating tumor-specific mutations or epigenetic changes. Relatively few of these markers have been defined in dogs compared to humans, but there are scattered reports of genetic mutations in non-lymphoid tumors from dogs, including C-terminal mutations of PTEN tumor suppressor gene in hemangiosarcomas, internal tandem repeats of c-kit in canine mast cell tumors, K-ras mutations in canine lung tumors, and p53, Rb and MDM2 mutations in several types of tumors including osteosarcomas and mammary carcinomas, and mutations of phosphatase and tensin homolog deleted from chromosome 10 in hemangiosarcoma (47-51). It is therefore, within the contemplated scope of the methods described herein that evaluation of these mutations can also be useful for determination of the diagnosis and/or prognosis of canines with non-lymphoid tumors.

There is also provided a method for measuring circulating DNA in order to monitor for residual disease and relapse. In another aspect, there is provided a method for evaluating whether circulating DNA levels decrease during treatment and increase at relapse. The method is useful to evaluate canines using a longitudinal study following plasma DNA levels in dogs before treatment, during remission, and during relapse. If it can be shown that circulating DNA levels fall during remission and increase before clinical detection of relapse, then this assay could be useful in earlier recognition of relapse and earlier therapeutic intervention.

A substantial portion of canines with lymphoid neoplasia have increased amounts of circulating DNA compared to healthy controls. Furthermore, increased plasma DNA is associated with shorter remission times regardless of clinical substage in dogs with lymphoid neoplasia. These results show that human and canine cancers exhibit similar fundamental biological characteristics.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

REFERENCES

The references discussed above and the following references, to the extent that they provide exemplary procedural or other details supplementary to those set forth herein, are specifically incorporated herein by reference.

(1) Dutra F R. Common neoplasms of pet animals. The Western Journal of Medicine 1978; 128:50.
(2) London C A, Hannah A L, Zadovoskaya R Chien M B, Kollias-Baker C, Rosenberg M, Downing S, Post G, Boucher J, Shenoy N, Mendel D B, McMahon G, Cherrington J M. Phase I dose-escalating study of SU11654, a small molecule receptor tyrosine kinase inhibitor, in dogs with spontaneous malignancies. Clinical Cancer Research 2003; 9:2755-2768.
(3) Bergman P J, McKnight J, Novosad A, Charney S, Farrelly J, Craft D, Wúlderk M, Jeffers Y, Sadelain M, Hohenhaus A E, Segal N, Gregor P, Engelhorn M, Riviere I, Houghton A N, Wolchok J D. Long-term survival of dogs with advanced malignant melanoma after DNA vaccination with xenogeneic human tyrosinase: a phase I trial. Clinical Cancer Research 2003; 9:1284-1290.
(4) Hansen K, Khanna C. Spontaneous and genetically engineered animal models; use in preclinical cancer drug development. European Journal of Cancer 2004; 40:858-880.
(5) Gautschi O, Bigosch C, Huegli B, Jermann M, Marx A, Chasse E, Ratschiller D, Weder W, Joerger M, Betticher D C, Stahel R A, Ziegler A. Circulating deoxyribonucleic acid as prognostic marker in non-small-cell lung cancer patients undergoing chemotherapy. Journal of Clinical Oncology 2004; 22:4157-4164.
(6) Ren N, Qin L X, Tu H, Liu Y K, Zhang B H, Tang Z Y. The prognostic value of circulating plasma DNA level and its allelic imbalance on chromosome 8p in patients with hepatocellular carcinoma. Journal of Cancer Research and Clinical Oncology 2006; 132:399-407.
(7) Jahr S, Hentze H, Englisch S, Hardt D, Fackelmayer F O, Hesch R D, Knippers R. DNA fragments in the blood plasma of cancer patients: quantitations and evidence for their origin from apoptotic and necrotic cells. Cancer Research 2001; 61:1659-1665.
(8) Weaver K D, Grossman S A, Herman J G. Methylated tumor-specific DNA as a plasma biomarker in patients with glioma. Cancer Investigation 2006; 24:35-40.
(9) Taback B, O'Day S J, Hoon D S. Quantification of circulating DNA in the plasma and serum of cancer patients. Annals of the New York Academy of Sciences 2004; 1022: 17-24.
(10) Wu T L, Zhang D, Chia J H, Tsao K H, Sun C F, Wu J T. Cell-free DNA: measurement in various carcinomas and establishment of normal reference range. Clinica Chimica Acta 2002; 321:77-87.
(11) Schlechte H H, Stelzer C, Weickmann S, Fleischhacker M, Schulze G. TP53 gene in blood plasma DNA of tumor patients. Annals of the New York Academy of Sciences 2004; 1022:61-69.
(12) Deligezer U, Yaman F, Erten N, Dalay N. Frequent copresence of methylated DNA and fragmented nucleosomal DNA in plasma of lymphoma patients. Clinica Chimica Acta 2003; 335:89-94.
(13) Esteller M, Sanchez-Cespedes M, Rosell R, Sidransky D, Baylin S B, Herman J G. Detection of aberrant promoter hypermethylation of tumor suppressor genes in serum DNA from non-small cell lung cancer patients. Cancer Research 1999; 59:67-70.
(14) Sorenson G D. A review of studies on the detection of mutated KRAS2 sequences as tumor markers in plasma/serum of patients with gastrointestinal cancer. Annals of the New York Academy of Sciences 2000; 906:13-16.
(15) Mulcahy H E, Lyautey J, Lederrey C, Qi-Chen X, Anker P, Alstead E M, Ballinger A, Farthing M J, Stroun M. A prospective study of K-ras mutations in the plasma of pancreatic cancer patients. Clinical Cancer Research 1998; 4:271-275.
(16) Diehl F, Li M, Dressman D, He Y, Shen D, Szabo S, Diaz L A, Goodman S N, David K A, Juhl H, Kinzler K W, Vogelstein B. Detection and quantification of mutations in the plasma of patients with colorectal tumors. Proceedings of the National Academy of Sciences of the United States of America 2005; 102:16368-16373.
(17) Muller H M, Fiegl H, Widschwendter A, Widschwendter M. Prognostic DNA methylation marker in serum of cancer patients. Annals of the New York Academy of Sciences 2004; 1022:44-49.
(18) Widschwendter A, Muller H M, Fiegl H, Ivarsson L, Wiedemair A, Muller-Holzner E, Goebel G, Marth C, Widschwendter M. DNA methylation in serum and tumors of cervical cancer patients. Clinical Cancer Research 2004; 10:565-571.
(19) Beau-Faller M, Gaub M P, Schneider A, Ducrocq X, Massard G, Gasser B, Chenard M P, Kessler R, Anker P, Stroun M, Weitzenblum, E, Pauli G, Wihlm, J M, Quoix E, Oudet P. Plasma DNA microsatellite panel as sensitive and tumor-specific marker in lung cancer patients. International Journal of Cancer 2003; 105:361-370.
(20) Schwarzenbach H, Muller V, Stahmann N, Pantel K. Detection and characterization of circulating microsatellite-DNA in blood of patients with breast cancer. Annals of the New York Academy of Sciences 2004; 1022:25-32.
(21) Shaw J A, Smith B M, Walsh T, Johnson S, Primrose L, Slade M J, Walker R A, Coombes R C. Microsatellite alterations plasma DNA of primary breast cancer patients. Clinical Cancer Research 2000; 6:1119-1124.
(22) Sozzi G, Conte D, Mariani L, LoVullo S, Roz L, Lombardo C, Pierotti M A, Tavecchio L. Analysis of circulating tumor DNA in plasma at diagnosis and during follow-up of lung cancer patients. Cancer Research 2001; 61:46754678.
(23) Frickhofen N, Muller E, Sandherr M, Binder T, Bangerter M, Wiest C, Enz M, Heimpel H. Rearranged Ig heavy chain DNA is detectable in cell-free blood samples of patients with B-cell neoplasia. Blood 1997; 90:49534960.
(24) Chan A T, Lo Y M, Zee B, Chan L Y, Ma B B, Leung S F, Mo F, Lai M, Ho S, Huang D P, Johnson P J. Plasma Epstein-Barr virus DNA and residual disease after radiotherapy for undifferentiated nasopharyngeal carcinoma. Journal of the National Cancer Institute 2002; 94:1614-1619.
(25) Rogers A, Joe Y, Manshouri T, Dey A, Jilani I, Giles F, Estey E, Freireich E, Keating M, Kantarjian H, Albitar M. Relative increase in leukemia-specific DNA in peripheral blood plasma from patients with acute myeloid leukemia and myelodysplasia. Blood 2004; 103:2799-2801.

(26) Galeazzi M, Morozzi G, Piccini M, Chen J, Bellisai F, Fineschi S, Marcolongo R. Dosage and characterization of circulating DNA: present usage and possible applications in systemic autoimmune disorders. Autoimmunity Reviews 2003; 2:50-55.

(27) Rainer T H, Lam N Y, Man C Y, Chiu R W, Woo K S, Lo Y M. Plasma beta-globin DNA as a prognostic marker in chest pain patients. Clinica Chimica Acta 2006.

(28) Chiu T W, Young R, Chan L Y, Burd A, Lo D Y. Plasma cell-free DNA as an indicator of severity of injury in burn patients. Clinical Chemistry and Laboratory Medicine 2006; 44:13-17.

(29) Martins G A, Kawamura M T, Carvalho M G. Detection of DNA in the plasma of septic patients. Annals of the New York Academy of Sciences 2000; 906:134-140.

(30) Makitie A A, Reis P P, Irish J, Zhang T, Chin S F, Chen X, Marriott C, Keller A, Perez-Ordonez B, Kamel-Reid S, Siu L L. Correlation of Epstein-Barr virus DNA in cell-free plasma, functional imaging and clinical course in locally advanced nasopharyngeal cancer: a pilot study. Head and Neck 2004; 26:815-822.

(31) Hochberger S, Althof D, de Schrott R G, Nachbaur N, Rock H, Leying H. Fully automated quantitation of Hepatitis B virus (HBV) DNA in human plasma by the COBAS AmpliPrep/COBAS TaqMan System. Journal of Clinical Virology 2006; 35:373-380.

(32) Lo Y M. Fetal DNA in maternal plasma. Annals of the New York Academy of Sciences 2000; 906:141-147.

(33) Garcia-Olmo D C, Gutierrez-Gonzalez L, Ruiz-Piqueras R, Picazo M G, Garcia-Olmo D. Detection of circulating tumor cells and of tumor DNA in plasma during tumor progression in rats. Cancer Letters 2005; 217:115123.

(34) Herrera L J, Raja S, Gooding W E, El-Hefnawy T, Kelly L, Luketich J D, Godfrey T E. Quantitative analysis of circulating plasma DNA as a tumor marker in thoracic malignancies. Clinical Chemistry 2005; 51:113-118.

(35) Jung M, Klotzek S, Lewandowski M, Fleischhacker M, Jung K. Changes in concentration of DNA in serum and plasma during storage of blood samples. Clinical Chemistry 2003; 49:1028-1029.

(36) Singer V L, Jones L J, Yue S T, Haugland R P. Characterization of PicoGreen reagent and development of a fluorescence-based solution assay for double-stranded DNA quantitation. Analytical Biochemistry 1997; 249:228-238.

(37) Burnett R C, Vernau W, Modiano J F, Olver C S, Moore P F, Avery A C. Diagnosis of canine lymphoid neoplasia using clonal rearrangements of antigen receptor genes. Veterinary Pathology 2003; 40:32-41.

(38) Solberg H E. Establishment and use of reference values. In: Burtis C A, Ashwood E R, editors. Tietz Fundamentals of Clinical Chemistry. 4 ed. Philadelphia: W.B. Saunders Company; 1996. 182-191.

(39) Herman J G. Circulating methylated DNA. Annals of the New York Academy of Sciences 2004; 1022:33-39.

(40) Onions D E. A prospective survey of familial canine lymphosarcoma. Journal of the National Cancer Institute 1984; 72:909-912.

(41) Dorn C R, Taylor D O, Schneider R, Hibbard H H, Klauber M R. Survey of animal neoplasms in Alameda and Contra Costa Counties, California. II. Cancer morbidity in dogs and cats from Alameda County. Journal of the National Cancer Institute 1968; 40:307-318.

(42) Teske E, de Vos J P, Egberink H F, Vos J H. Clustering in canine malignant lymphoma. The Veterinary Quarterly 1994; 16:134-136.

(43) Leon S A, Shapiro B, Sklaroff D M, Yaros M J. Free DNA in the serum of cancer patients and the effect of therapy. Cancer Research 1977; 37:646650.

(44) Zander D S, Iturraspe J A, Everett E T, Massey J K, Braylan R C. Flow cytometry. In vitro assessment of its potential application for diagnosis and classification of lymphoid processes in cytologic preparations from fine-needle aspirates. American Journal of Clinical Pathology 1994; 101:577586.

(45) Bertram H C, Check I J, Milano M A. Immunophenotyping large B-cell lymphomas. Flow cytometric pitfalls and pathologic correlation. American Journal of Clinical Pathology 2001; 116:191-203.

(46) Lana S E, Jackson T L, Burnett R C, Morley P S, Avery A C. Utility of polymerase chain reaction for analysis of antigen receptor rearrangement in staging and predicting prognosis in dogs with lymphoma. Journal of Veterinary Internal Medicine 2006; 20:329-334.

(47) Downing S, Chien M B, Kass P H, Moore P E, London C A. Prevalence and importance of internal tandem duplications in exons 11 and 12 of c-kit in mast cell tumors of dogs. American Journal of Veterinary Research 2002; 63:1718-1723.

(48) Griffey S M, Kraegel S A, Madewell B R. Rapid detection of K-ras gene mutations in canine lung cancer using single-strand conformational polymorphism analysis. Carcinogenesis 1998; 19:959-963.

(39) Wakui S, Muto T, Yokoo K, Takahashi H, Masaoka T, Hano H, Furusato M. Prognostic status of p53 gene mutation in canine mammary carcinoma. Anticancer Research 2001; 21:611-616.

(50) Mendoza S, Konishi T, Dernell W S, Withrow S J, Miller C W. Status of the p53, Rb and MDM2 genes in canine osteosarcoma. Anticancer Research 1998; 18:4449-4453.

(51) Dickerson E B, Thomas R, Fosmire S P, Lamerato-Kozicki A R, Bianco S R, Wojcieszyn J W, Breen M, Helfand S C, Modiano J F. Mutations of phosphatase and tensin homolog deleted from chromosome 10 in canine hemangiosarcoma. Veterinary Pathology 2005; 42:618-632.

What is claimed is:

1. A method of evaluating the disease condition of a canine suspected of having or at risk of having a lymphoid neoplasia-related disease, the method comprising:
   (i) obtaining a sample of plasma from the canine suspected of having or at risk of having the lymphoid neoplasia-related disease;
   (ii) detecting the presence of plasma nucleic acid in the sample; and
   (iii) identifying the canine as having or at risk of having the lymphoid neoplasia-related disease when the level of the detected plasma nucleic acid is 25 ng/ml or greater.

2. The method of claim 1, wherein the plasma nucleic acid comprises one or more tumor-specific DNA markers selected from K-ras.

3. The method of claim 1, wherein the lymphoid neoplastic-related disease comprises lymphoma or leukemia.

4. A method for detecting a lymphoid neoplasia-related disease in a canine, the method comprising the steps of:
   (i) purifying extracellular nucleic acid from blood plasma from the canine to prepare extracted extracellular nucleic acid, and concurrently or sequentially,
   (ii) amplifying extracellular nucleic acid or a fragment thereof, or amplifying a signal from the extracellular nucleic acid or a fragment thereof; and
   (iii) detecting the product of the amplified extracellular nucleic acid or the product of its amplified fragment, or the amplified signal of the extracellular nucleic acid or the amplified signal of a fragment thereof; wherein the extracellular nucleic acid comprises a DNA encoding a mutated gene or fragment thereof;

(iv) identifying the canine as having lymphoid neoplasia when 25 ng/ml or greater of the mutated gene or fragment thereof is detected.

5. The method of claim 4, further including: enriching the extracted extracellular nucleic acid or a fragment thereof, wherein the nucleic acid or a fragment thereof is concentrated or isolated from the remaining extracted extracellular nucleic acid.

6. The method of claim 4, wherein the product of the amplified mutated gene DNA is detected using a detection method that comprises gel electrophoresis, single strand conformation polymorphism, heteroduplex analysis, denaturing gradient gel electrophoresis, mismatch cleavage assay, immunological detection methods, nucleic acid hybridization, Southern blot analysis, electrochemiluminescence, reverse dot blot detection, or high-performance liquid chromatography.

7. The method of claim 5, wherein the enriched mutated gene DNA or a fragment thereof is amplified using an amplification method that is polymerase chain reaction, ligase chain reaction, boomerang DNA amplification, Q-beta replication, transcription-based amplification, isothermal nucleic acid sequence based amplification, self-sustained sequence replication assay, strand displacement activation, or cycling probe technology.

8. A method of claim 5, wherein mutated gene DNA or a fragment thereof is enriched through an endonuclease-mediated restriction digestion, or by hybridization of the mutated gene DNA or a fragment thereof to an oligonucleotide to form a hybridized complex.

9. The method of claim 4, wherein the mutated gene is a mutated K-ras.

10. A method of identifying a canine having a lymphoid neoplastic disease without clinical symptoms comprising
    detecting an elevated level of 25 ng/ml or greater of extracellular nucleic acid from plasma DNA from the canine
    wherein the plasma DNA comprises a tumor-derived plasma DNA.

11. A method of claim 10, wherein an evaluation in the plasma DNA of at least a K-ras mutation assists in the identification of the disease or condition.

12. A method of claim 10, wherein an evaluation in the plasma DNA of at least a p53 mutation assists in the identification of the disease or condition.

13. A method of claim 10, wherein an evaluation in the plasma DNA of at least a Rb mutation assists in the identification of the disease or condition.

* * * * *

UNITED STATES PATENT AND TRADEMARK OFFICE
CERTIFICATE OF CORRECTION

PATENT NO. : 7,745,132 B1
APPLICATION NO. : 11/998155
DATED : June 29, 2010
INVENTOR(S) : Laura J. Rush It is certified that error appears in the above-identified patent and that said Letters Patent is hereby corrected as shown below:

Claim 1, Column 16, line 2, after "having" insert -- , known to have, -- and after "or at risk of having" insert -- , --.
Column 16, line 5, after "of having" first occurence insert -- , -- and after "of having" second occurence insert -- , --.
Column 16, line 9, after "having" insert -- , --.

Claim 2, Column 16, line 3, after "from" insert -- the group consisting of --.
Column 16, line 3, after "K-ras" insert -- , p53 and Rb --.

Claim 4, Column 16, line 1, after "detecting" insert -- in a canine --.
Column 16, line 2, after "disease" insert -- , -- and remove "in a canine,".

Claim 9, Column 18, lines 1 and 2, remove the entire claim and insert -- The method of Claim 4, wherein the mutated gene is selected from the group consisting of a mutated K-ras, a mutated P53 or a mutated Rb. --.

Signed and Sealed this

Twelfth Day of October, 2010

David J. Kappos
*Director of the United States Patent and Trademark Office*

UNITED STATES PATENT AND TRADEMARK OFFICE
CERTIFICATE OF CORRECTION

PATENT NO.        : 7,745,132 B1                                              Page 1 of 1
APPLICATION NO.   : 11/998155
DATED             : June 29, 2010
INVENTOR(S)       : Laura J. Rush It is certified that error appears in the above-identified patent and that said Letters Patent is hereby corrected as shown below:

Column 16, line 43, (claim 1, line 2) after "having" insert -- , known to have, -- and after "or at risk of having" insert -- , --.
Column 16, line 46, (claim 1, line 5) after "of having" first occurence insert -- , -- and after "of having" second occurence insert -- , --.
Column 16, line 50, (claim 1, line 9) after "having" insert -- , --.

Column 16, line 55, (claim 2, line 3) after "from" insert -- the group consisting of --.
Column 16, line 55, (claim 2, line 3) after "K-ras" insert -- , p53 and Rb --.

Column 16, line 58, (claim 4, line 1) after "detecting" insert -- in a canine --.
Column 16, line 59, (claim 4, line 2) after "disease" insert -- , -- and remove "in a canine,".

Column 18, lines 9 and 10, (claim 9, lines 1 and 2) remove the entire claim and insert -- The method of Claim 4, wherein the mutated gene is selected from the group consisting of a mutated K-ras, a mutated P53 or a mutated Rb. --.

This certificate supersedes the Certificate of Correction issued October 12, 2010.

Signed and Sealed this

Ninth Day of November, 2010

David J. Kappos
*Director of the United States Patent and Trademark Office*